(12) United States Patent
Bertocci

(10) Patent No.: US 8,292,830 B2
(45) Date of Patent: Oct. 23, 2012

(54) SOFT TISSUE IMPACT ASSESSMENT DEVICE AND SYSTEM

(75) Inventor: Gina Bertocci, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 81 days.

(21) Appl. No.: 12/154,166

(22) Filed: May 21, 2008

(65) Prior Publication Data

US 2008/0289438 A1    Nov. 27, 2008

Related U.S. Application Data

(60) Provisional application No. 60/931,203, filed on May 22, 2007.

(51) Int. Cl.
  *A61B 5/103* (2006.01)
  *A61B 5/117* (2006.01)
  *A61B 19/00* (2006.01)
  *A61B 5/04* (2006.01)
  *A61B 5/00* (2006.01)
(52) U.S. Cl. ........... 600/587; 600/553; 600/388; 73/172
(58) Field of Classification Search ............. 600/372, 600/382, 388, 393, 553, 587; 434/262, 267, 434/274; 73/172, 379.04, 866.4
See application file for complete search history.

(56) References Cited

U.S. PATENT DOCUMENTS

| | | | |
|---|---|---|---|
| 3,818,756 A * | 6/1974 | Barron et al. | 73/172 |
| 4,691,556 A * | 9/1987 | Mellander et al. | 73/12.01 |
| 4,824,107 A * | 4/1989 | French | 273/454 |
| 5,375,397 A * | 12/1994 | Ferrand et al. | 54/66 |
| 5,628,230 A * | 5/1997 | Flam | 73/172 |
| 5,648,915 A | 7/1997 | McKinney | |
| 6,752,770 B2 * | 6/2004 | Mayrose et al. | 600/587 |

(Continued)

OTHER PUBLICATIONS

TEKSCAN Brochure.

(Continued)

*Primary Examiner* — Jeffrey G. Hoekstra
*Assistant Examiner* — Devin Henson
(74) *Attorney, Agent, or Firm* — Greer, Burns & Crain Ltd.

(57) ABSTRACT

An embodiment of the invention is a soft tissue impact assessment device. The device includes a skin that is shaped or moldable to a human-like form. A positional force or pressure sensor within the skin measures force or pressure and location of impact or contact with the skin and provides data regarding the force or pressure and location of impact or contact with the skin. In preferred embodiments, the skin includes a top layer made of a material and thickness that simulates the protection provided by particular human skin to underlying tissue. A pressure or force sensor sheet closely contacts the top layer in a manner that avoids any substantial movement between the top layer and the pressure or force sensor sheet during a range of anticipated force or pressure conditions to be experienced by the human surrogate during testing. A lining layer is suitable to be in close contact with a surface of a human like form. A preferred method for assessing potential for soft tissue injuries is implemented in software and includes accepting victim or human subject soft tissue injury data being assessed and comparing it to a database including objective data to determine compatibility between the stated cause of event and resulting soft tissue injuries. The database in preferred embodiments includes information organized by category of potentially injurious events, human age, and objective data relating magnitude of force or pressure, and location of impact(s) or contact(s) relative to various body regions.

21 Claims, 4 Drawing Sheets

U.S. PATENT DOCUMENTS

| | | | |
|---|---|---|---|
| 6,925,851 B2 * | 8/2005 | Reinbold et al. | 73/12.09 |
| 6,964,205 B2 * | 11/2005 | Papakostas et al. | 73/862.046 |
| 2003/0066365 A1 * | 4/2003 | Biermann et al. | 73/866.4 |
| 2004/0122702 A1 | 6/2004 | Sabol et al. | |
| 2005/0126258 A1 | 6/2005 | Lipmyer | |

OTHER PUBLICATIONS

"Intellectual Dummies", *Transportation*, pp. 70-71.

* cited by examiner

SOFT TISSUE IMPACT ASSESSMENT DEVICE AND SYSTEM

PRIORITY CLAIM AND REFERENCE TO RELATED APPLICATION

The application claims priority under 35 U.S.C. §119 from prior provisional application Ser. No. 60/931,203, which was filed May 22, 2007.

FIELD

A field of the invention is injury risk assessment using anthromorphic test devices, i.e., simulating and evaluating injuries that would be experienced by a human subject under particular conditions. Example applications of the invention include automotive crash safety testing, simulation and evaluation of abusive and non-abusive injuries in the human population, particularly in the elderly and child population.

BACKGROUND

Assessment of human injury risk is an important step in the design of many products. As a well-known example, the automotive industry conducts extensive testing to determine likely human injury risk experienced during automobile crashes. The industry has evolved from cadaver studies to the use of increasingly sophisticated anthropomorphic test devices (crash test dummies or human surrogates) that provide data on injury outcome measuring how human bodies react in crashes. The use of such dummies is primarily concerned with severe injuries and provides injury outcome measurement data to allow for the assessment of injury risk (e.g., fractured bones or severe head injuries). Currently, dummies provide little or no data on the risk of soft tissue bruising and/or contusion injuries.

An issue of social and forensic importance is the evaluation of less severe injuries, particularly among the elderly and children. Hospitals, agencies and courts are presented with a pattern of injuries experienced by children and elderly persons, for example, and must determine whether or not the injuries were the result of accident or abuse. Identification of bruising patterns, and/or points of contact/impact on the body, provides a roadmap of a person's exposure to force application and documents points of impact. Practical systems that document impact points on the body for evaluating the likelihood of such injuries as bruising and/or contusions of soft tissues under various conditions could provide information to aid in the determination of whether the injuries are a result of abuse or accident.

SUMMARY OF THE INVENTION

An embodiment of the invention is a soft tissue impact assessment device. The device includes a skin that is shaped or moldable to a human-like form. An array of positional pressure or force sensors within the skin measures pressure or force and location of impact to the skin and provides data regarding the force or pressure and location of impact to the skin. In preferred embodiments, the skin includes flexible top and bottom layers that sandwich the sensor array that simulates the protection provided by human skin to underlying tissue. A force or pressure sensor array in the form of a sheet closely contacts the top and bottom layers in a manner that avoids any substantial movement between the layers and the pressure or force sensor array sheet during a range of anticipated conditions to be experienced during testing. A lining or bottom layer is suitable to be in close contact with a surface of the human-like form. The skin is preferably configured to closely fit around the human like form. In preferred embodiments, the human like form represents a human infant and human child.

A preferred method for using a soft tissue impact assessment device of the invention is to position the device, which can be referred to as a sensor skin, to encase a human-like form or test dummy and then conduct simulations of common events having the potential to produce injury. During these simulations, the sensor skin will measure the application of force or pressure as well as the location of impact or contact. Output from the soft tissue impact assessment device is transmitted to a data acquisition system and software program, which compiles the output data. The output data, including the magnitude of the force or pressure and the location of impact or contact are presented on a computerized body map image. This preferred method will allow for the documentation of bruising patterns associated with various conditions having the potential to produce injury. Knowledge of bruising patterns will aid in the forensic investigation of injuries suspected to have resulted from abuse.

Another embodiment of the invention is a database that includes a knowledge base of impact or contact patterns that represent potential bruising, associated with various injury producing scenarios or events. The database is generated based upon tests conducted using sensor skin of the invention adapted to a human surrogate or dummy. This database includes data to generate body image maps describing patterns and numbers of potential bruises or soft tissue injuries associated with specific events. The database in preferred embodiments includes data to generate soft tissue impact body image maps organized by category of injury events, human age, gender and anthropometric characteristics. The database can be queried to determine the compatibility between the stated cause of injury and the presenting soft tissue injuries.

DETAILED DESCRIPTION OF THE PREFERRED EMBODIMENTS

Figure 1:
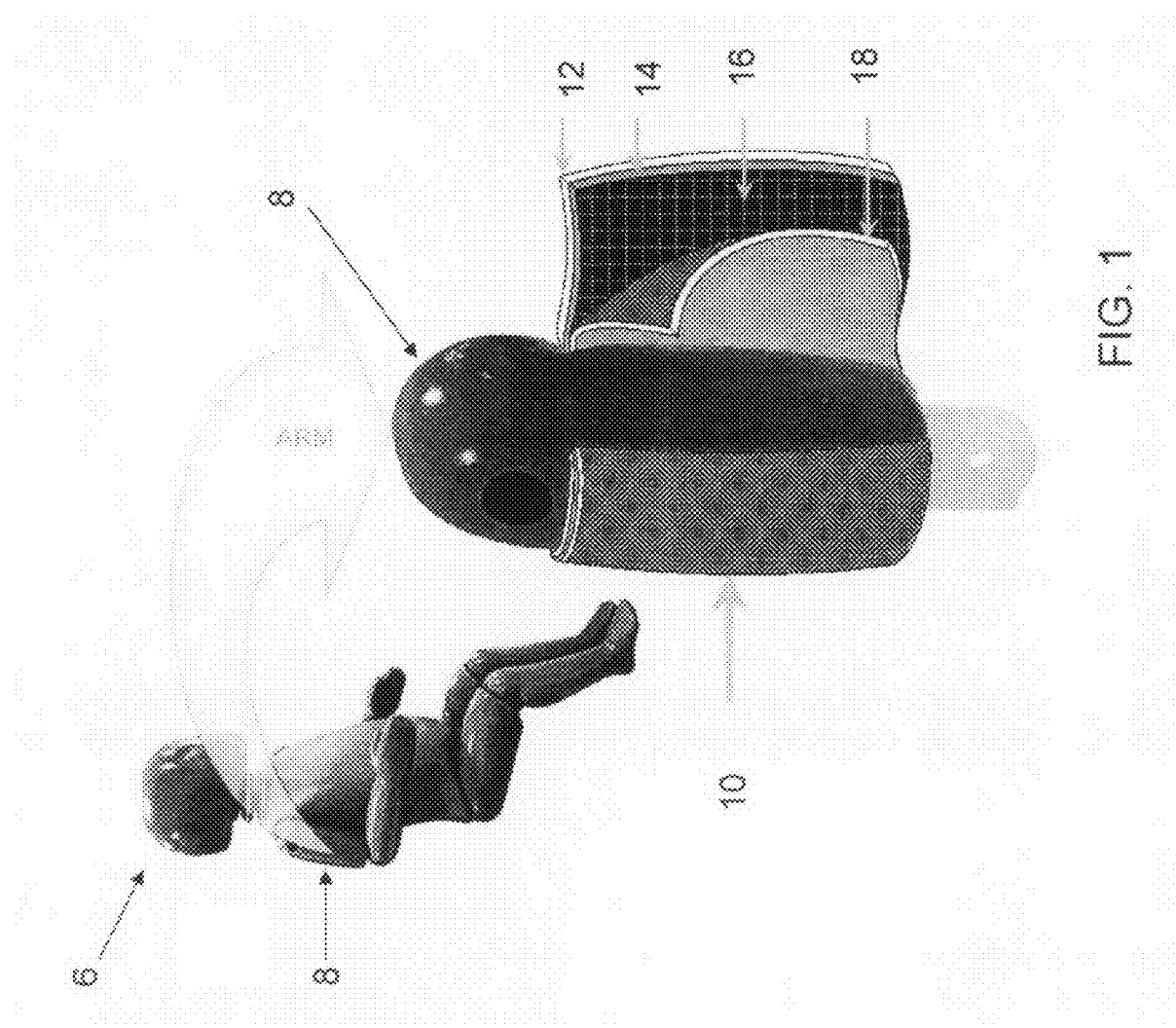
FIG. 1 is a schematic drawing of a soft tissue impact assessment device sensor skin in accordance with an embodiment of the invention.

An embodiment of the invention is a soft tissue impact assessment device. The device includes a sensor skin that is shaped or moldable to a human-like form. An array of positional force or pressure sensors within the skin measures force or pressure and location of impact or contact with the skin and provides corresponding output data regarding the magnitude of pressure or force and location of impact or contact with the skin. In preferred embodiments, the skin includes flexible top and bottom layers that sandwich the sensor array that simulates the protection provided by human skin to underlying tissue. A force or pressure sensor array in the form of a sheet closely contacts the top and bottom layers in a manner that avoids any substantial movement between the protective layers and the pressure or force sensor array sheet during a range of anticipated conditions to be experienced during testing. A lining or bottom layer is suitable to be in close contact with a surface of the human-like form. The skin is preferably configured to closely fit around the human like form. In preferred embodiments, the human like form represents a human infant and human child. A database including a knowledge base of impact or contact patterns that would represent potential bruising associated with various injury producing scenarios or events is generated based upon tests conducted using the sensor skin adapted to a human surrogate or dummy. This database includes data to generate body image maps describing patterns and numbers of potential bruises or soft tissue injuries associated with specific events. The database in preferred embodiments includes data to generate soft tissue impact body image maps organized by category of injury events, human age, gender and anthropometric characteristics. The database can be queried to determine the compatibility between the stated cause of injury and the presenting soft tissue injuries.

An embodiment of the invention is a sensor "skin" that can be placed over a human surrogate or portion of a human surrogate to record an impact or contact to the body. The sensor skin identifies, and can record, points of contact and impact. In a preferred embodiment, the sensor skin includes an array of pressure or force sensors that provide pressure or force data along with the location or region of impact. A system of the invention can include a graphical readout on a display of the magnitude of impact, which can also preferably be color coded to the level or range of force or pressure in a specific body region.

In preferred embodiments, the skin envelops the human-like form or surrogate, e.g., a dummy. A preferred embodiment is a multi-use device that includes a skin formed with a matrix or array of moldable sensors, such as a commercially available system from TekScan, of Boston, Mass., and circuitry integrated with the skin to provide location and level or range of force or pressure experienced by the skin.

Another preferred embodiment is a dummy, in a human form, that includes a network of pressure or force sensors covering a substantial portion of an outer skin of the dummy. The pressure or force sensors measure force or pressure and location of impact with the skin and provide data regarding the force or pressure and location of impact against the skin. The data can be a visible indication, such as a color indicative of a level of force, or the data can be a data signal. In preferred embodiments, memory and circuitry in the skin are incorporated to maintain or record impact or contact location, and force or pressure magnitude data to permit the obtainment of a record of soft tissue contacts or impacts experienced by multiple events. In preferred embodiments, the sensor skin includes an output interface, such as a wired connection port, or wireless communication abilities to transmit obtained impact location, and force or pressure data of event to a computer software system that will compile the data and represent it in a body map image.

In another preferred embodiment, a conventional dummy or human surrogate is retrofitted with an outer sensor skin. The skin includes a network of pressure or force sensors within or upon a substantial portion of the skin. The sensors measure force or pressure and location of impact or contact with the skin and provide data regarding the force or pressure and location of impact or contact with the skin. The data can be an electronic or digital output. In preferred embodiments, memory and circuitry in the skin are incorporated to maintain or record impact or contact location, and force or pressure magnitude data to permit the obtainment of a record of soft tissue contacts or impacts experienced by multiple events. In preferred embodiments, the sensor skin includes an output interface, such as a wired connection port, or wireless communication abilities to transmit obtained impact location, and force or pressure data of event to a computer software system that will compile the data and represent it in a body map image. Preferred embodiment sensor skin devices of the invention are calibrated and shaped toward specific forms. An example embodiment is shaped and calibrated to record a contact or impact to that which would be experienced by human soft tissue of an infant, child or adult. Preferred embodiment secondary systems include interfaces that receive force or pressure data from a sensor skin of the invention and store it in a data structure that maintains positional information relative to body regions and information to identify the test skin that the force response data was generated from, e.g., a serial number and/or characteristic morphological information about the particular sensor skin and the location of force or pressure data (e.g., human surrogate anthropometric size, location of right upper outer arm, magnitude level X) concerning the particular sensor skin that the data was generated from. The secondary system in preferred embodiments also includes a display system that displays a model of the sensor skin mapped to human surrogate body or shape that experienced impact and provides an indication in the display of the location and magnitude of the impacts or contacts experienced by the sensor skin.

Another preferred embodiment of the invention is a database generated from data of a preferred embodiment sensor skin. The database is searchable by type of injury event. For example, the database can be queried for "fall down stairs", or "fall out of crib", etc. Additionally, the database can be queried for age of subject matching test dummy availability, e.g., "toddler", 6 year old child, small female. Data sets are developed from sensor skins under like conditions and for comparable human-surrogate models. In preferred embodiments, after an appropriate query, the system outputs to a user information showing the likely contact locations and associated levels of force or pressure resulting from a specific event. The output is preferably a graphical display illustrating, e.g., a human form and the location and presence of contact points that may lead to bruising/contusions from a particular type of event that was queried. The information is presented to aid a user, for example a judge, hospital worker, police officer, social worker, etc. to determine whether particular soft tissue injury patterns in a human subject are consistent with a stated accident scenario, for example.

Preferred embodiments of the invention will now be discussed with respect to the drawings. The drawings may include schematic representations, which will be understood by artisans in view of the general knowledge in the art and the description that follows. Features may be exaggerated in the drawings for emphasis, and features may not be to scale.

Figure 2:
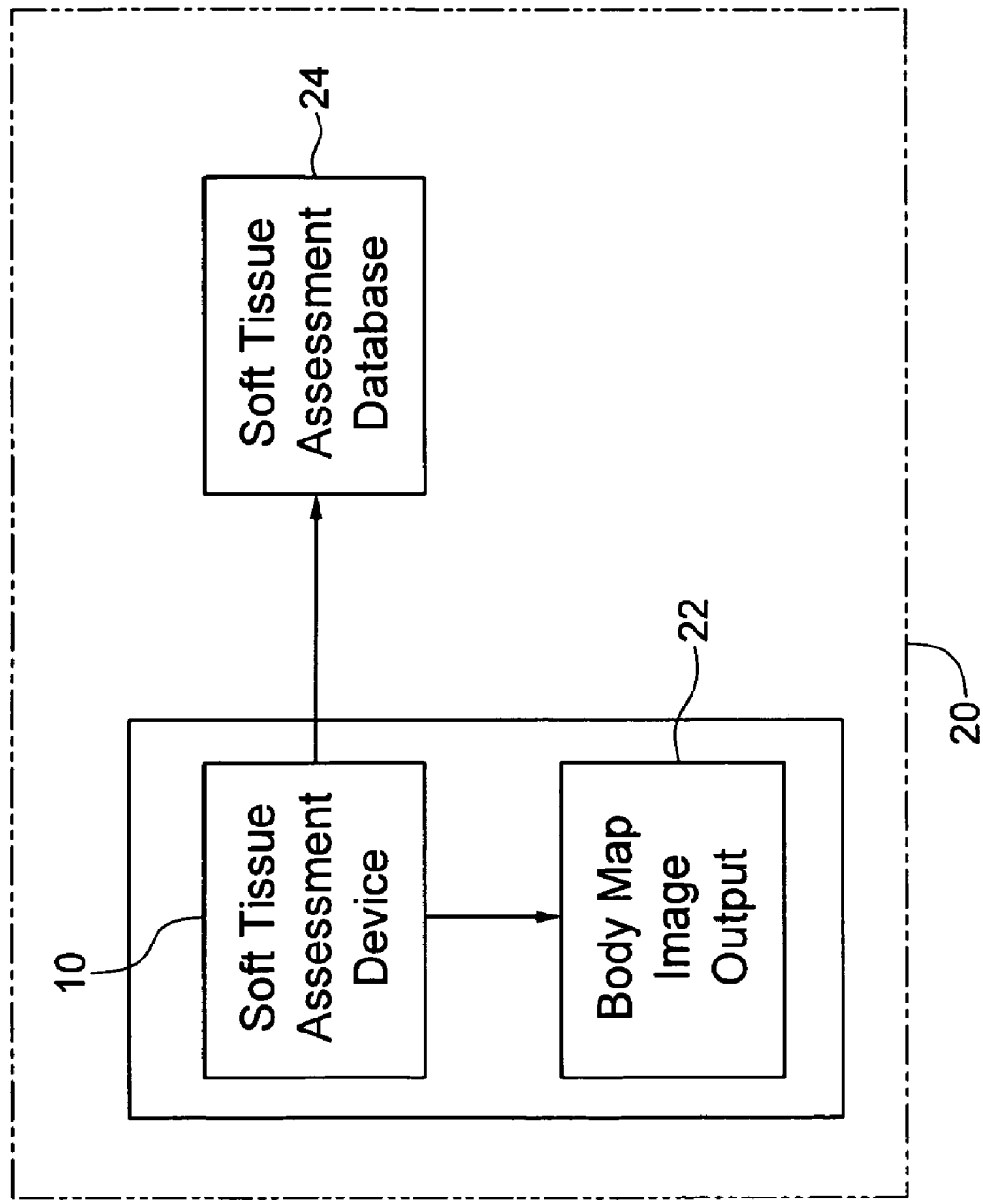
FIG. 2 shows a preferred embodiment system for the assessment of soft tissue impacts.

A preferred soft tissue impact assessment device is provided in FIG. 2. A human infant dummy or surrogate 6, and particularly an upper arm 8 of the dummy or surrogate 6 provides a shape that a soft tissue impact device 10 closely molds to and surrounds, is illustrated in FIG. 2. The sensor skin 10 is illustrated as being formed from multiple layers, but the sensor skin 10 can also be formed as single integrated structure. Multiple layers form one structural embodiment, but there is no reason that the layers cannot be combined into an integrated device that performs the separate functions of the preferred embodiment device 10.

In the illustrated embodiment, a top layer 12 is preferably formed of neoprene of a thickness that simulates the protection provided by particular human skin to underlying tissue, for example the arm area of a human infant in the example of FIG. 1. Other materials that can simulate the protection offered by particular human skin can also be used. The soft tissue impact assessment device 10, also preferably simulates the shape and texture of skin at a particular location, and can be referred to as a sensor skin. In preferred embodiments, as illustrated in FIG. 1, the entire device 10 preferably closely wraps around a portion of a human-like form. In the example of FIG. 1, the device 10 fits closely around and surrounds a portion, i.e., the upper arm 8, of the human like form of the test dummy 6, which is configured as a human infant. The material selected for the top layer 12 should conduct force or pressure from impact through the top layer 12 in the same manner as the particular skin the top layer 12 is intended to simulate.

The next layer of the preferred soft tissue impact assessment device 10 is a pressure or force sensor sheet 14. The pressure sensor sheet is preferably fixedly attached or adhered to the top layer 12 to avoid any substantial movement between the top layer and the sensor sheet 14 during the range of anticipated impact or contact conditions to be experienced during testing. Press-fitting, friction surfaces, close tolerances or the like can take the place of adhesion or other attachment so long as substantial movement between the top layer 12 and the sensor sheet 14 is avoided during the range of anticipated impact or contacting conditions to be experienced during testing. The pressure or force sensor sheet 14 can include an array of pressure or force sensors 16, or it can also comprise a continuous pressure sensitive film. The preferred sensor sheet 14 with its sensor array 16, can also be integrally molded to the top layer 12 and the other layers that are illustrated. A lining layer 18 is also formed of neoprene or material suitable to be in close contact with a surface of a human surrogate or human-like form. In preferred embodiments made of neoprene, the top layer 12 and the lining layer 18 are approximately 1.5 mm thick. This layer approximates human infant skin for testing when the soft tissue impact assessment device 10 is mounted or contoured to the test dummy.

The pressure or force sensor array 16 provides data regarding the force and location of impact for output. The sensors 16 are preferably assigned unique values corresponding to their position location. In the example of FIG. 1, where the device 10 is configured to be placed on the arm of the human infant, the positional values of the sensors map to locations on the arm of the human infant.

During testing, the forces or pressures measured by sensors in a particular area or areas can provide a "footprint" or "map" of the impact or contact. The positional locations assigned to the sensors 16 and their corresponding mapping permits the generation of graphical outputs/images that illustrate the result of a test event.

In certain embodiments of the invention, it is contemplated that the sensor skin can be wrapped such that the "skin" of a crash test dummy is composed of the soft tissue impact assessment device to form a dummy with a sensor skin of the invention. It is contemplated that the entire device 10 of FIG. 2 can form the skin of a test dummy. The dummy can be manufactured with the device 10 as its skin. Alternatively, existing crash test dummies or human surrogates can be retrofitted to include the present soft tissue impact assessment device such that the device is affixed or adhered to an existing crash test dummy. In this way, the sensor skin can be added to a crash test dummy or human surrogate to fully cover an appendage or body such that there is one seam. It is also contemplated that portions of the sensor skin may be added to specific portions of a crash test dummy, such that only the portion of interest for a specific test is covered with the sensor skin.

FIG. 2 shows a preferred embodiment system 20 for the assessment of a soft tissue impact. The system of FIG. 2 includes the soft tissue impact assessment device 10 of FIG. 1. An output device 22 displays information based on the force or pressure and location of the impact or contact with the skin. The output device can be a programmed general purpose computer. In preferred embodiments, the output includes body map images that represent locations of contact and force or pressure magnitude at these locations. A database 24 is created and maintained from information measured based on the force or pressure and location of the impact or contact with the sensor skin in accordance with the device 10 of FIG. 1 Testing can be conducted to collect data relating to specific types of impacts or contacts caused by particular events.

A preferred embodiment of the database 24 is searchable by type of injury event. For example, the database can be queried for "fall down stairs", or "fall out of crib", etc. Additionally, the database can be queried for age of subject, e.g., "toddler", "adult". Data sets are developed from devices 10 of the invention under like conditions and for comparable human-like surrogate models. A query is answered with information that preferably includes an image that shows the location of the likely soft tissue injuries caused by a specific event. This information is especially important in models developed for infants, children and the elderly. Information derived from sensor devices used to build the soft tissue injury database provides objective information that is not readily available.

By way of further example, the type of information returned by a query can include images and textual descriptions showing the likely contact locations and level of force or pressure resulting from a specific event. The output is preferably a graphical display illustrating, e.g., a body or body region form and the location and presence of contact points that may lead to bruising/contusions from a particular type of event that was queried. The information is presented to aid a user, for example a judge, hospital worker, police officer, social worker, etc. to determine whether particular injuries in a human subject are consistent with the specified accident scenario, for example.

The sensor sheet 14 of the device 10 in the system 20 can communicate with the output device 22 wirelessly or via a wired connection. Standard data communication techniques and protocols can be used. An example connection method uses one of the 802.11 protocols; other methods include a Bluetooth® connection or a wired connection such as through a USB cable. The output device 22 preferably includes an interactive graphical user interface, permitting a user to interact and manipulate models showing likely impact or contact points associated with a particular event, for a given human surrogate age.

Figure 3:
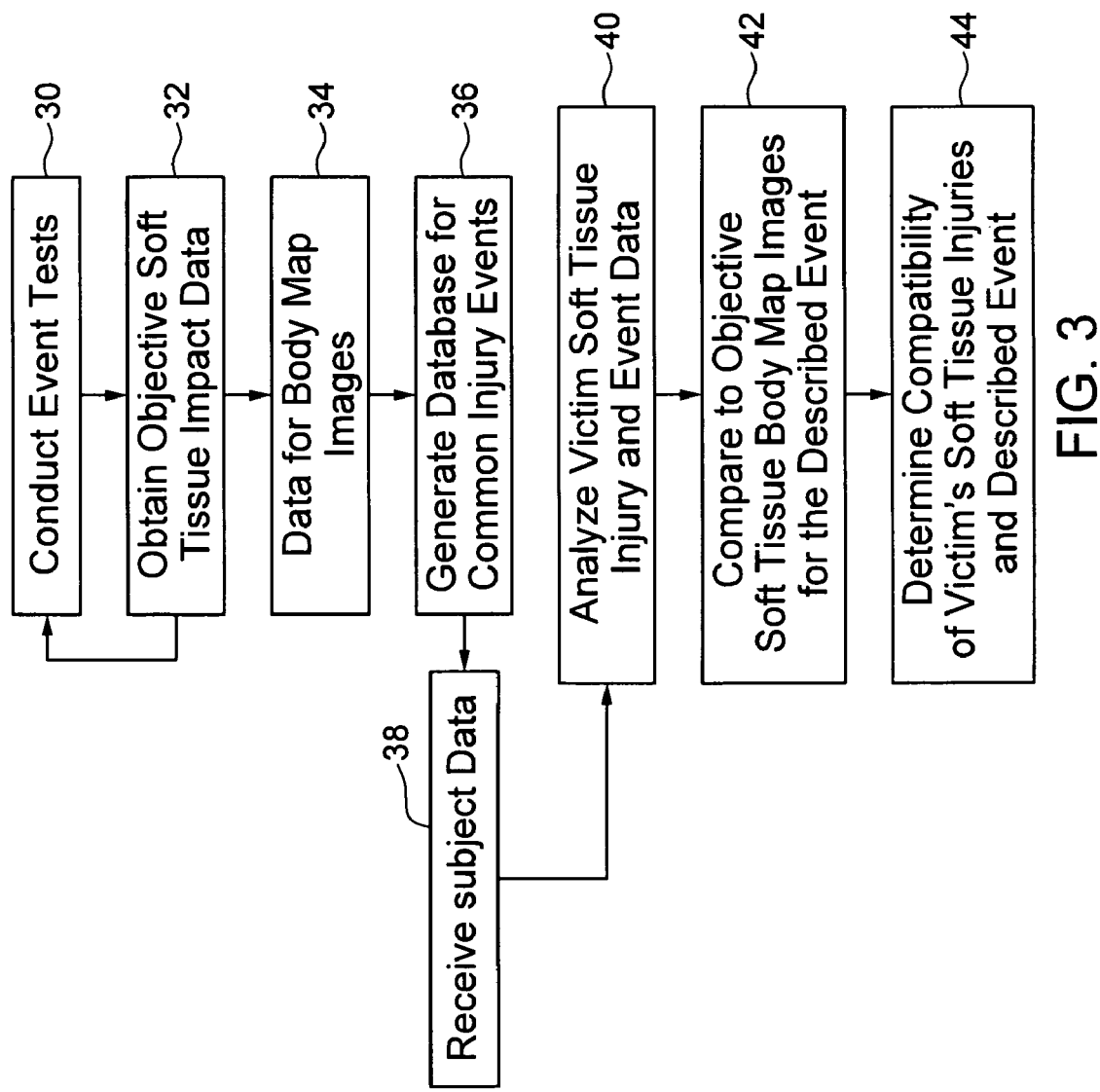
FIG. 3 illustrates a preferred embodiment method of the invention for assessing soft tissue impacts.

A method for assessing compatibility of soft tissue injuries presenting in a human subject and the stated cause of the soft tissue injuries is also provided by the invention. A preferred embodiment method of the invention is illustrated in FIG. 3. The method is preferably implemented in software, and makes use of a data from a database 24 of the invention.

Preliminary steps of creating the database involve obtaining objective data from event tests 30 using a crash test dummy or human surrogate equipped with a soft tissue impact assessment device 10 of the invention. Tests are repeated multiple times under controlled conditions to obtain the objective soft tissue impact data 32. From the multiple tests, data is collected that permits the generation of body map images 34 are generated identifying the impact force or pressure and impact location information for each event type for a given human surrogate. Different database tables 36 can be constructed or indexed for specific groups or categories of human surrogates, for example, a pediatric database and/or a geriatric database, or for a various event types. This database can be directed to having information regarding impacts with regard to those specific groups.

Subject data is then received 38. Entry of the data can include manual entry after tests are conducted on a subject, or it can include receiving information from an interface created with device or system being used to measure the subject. The data that is entered preferably characterizes the soft tissue at the point of impact, and can be obtained by ultrasound, x-rays, tomography, etc. Once the soft tissue injuries of the human subject are compiled they are analyzed 40 by comparison to the body map image data that exists in the database for the specified similar event. The analysis can include a comparison 42 of subject data to objective soft tissue body map data/images for the described event. The comparison can be electronic, such as by image analysis, or can be conducted visually by an expert, such as a forensic expert. Compatibility of the human subject or victim's soft tissue injuries with the stated event or cause of injury is determined 44 from the comparison.

As an example, the preliminary steps 30 and 32 can be created using a crash test dummy or human surrogate of an infant having the device 10 of FIG. 2. A number of varying events leading to contact or impact of the sensor skin may be assessed using the device 10 and the information regarding the force or pressure and the location of each of the impacts or contacts is saved as body image maps in the database tables. The database is accessed when, for example, an infant having soft tissue injuries is suspected of being subjected to abuse. The soft tissue injuries present on the infant are compiled and recorded in a graphic body map image format. Once the soft tissue injuries are summarized, the actual soft tissue injuries are compared in step 42 and compatibility with the stated cause or event is described in step 44. The software can provide or aid in the determination of the compatibility between the stated event and the presenting soft tissue injuries identifying differences between the actual contact points on the human and those determined through experimental tests using the soft tissue assessment device 10. For example, falling from a bed may generate a specific roadmap of soft tissue injuries in terms of location, number and size, whereas the roadmap generated with a stair fall may be different and unique.

A preferred method implemented by software for assessing soft tissue impact potential includes obtaining objective data concerning human soft tissue injuries for different categories of injury events and for different human age, gender and anthropometric characteristics. A database of the objective data is maintained. Queries to the database with subject soft tissue data relating to a human injury being assessed are accepted. The objective data is searched to match the subject soft tissue data to particular categories of likely events that could lead to the injuries indicated by the subject soft tissue data are outputted. In preferred embodiments, the database is accessible as a fee or subscription service to medical institutions.

For example, the impact "footprint" or "map" may be consistent with an injury such as falling down stairs or being struck with a certain amount of force. In this way, the medical staff can determine the type of injury that has occurred to the infant and can better plan a course of treatment of the infant.

Figure 4:
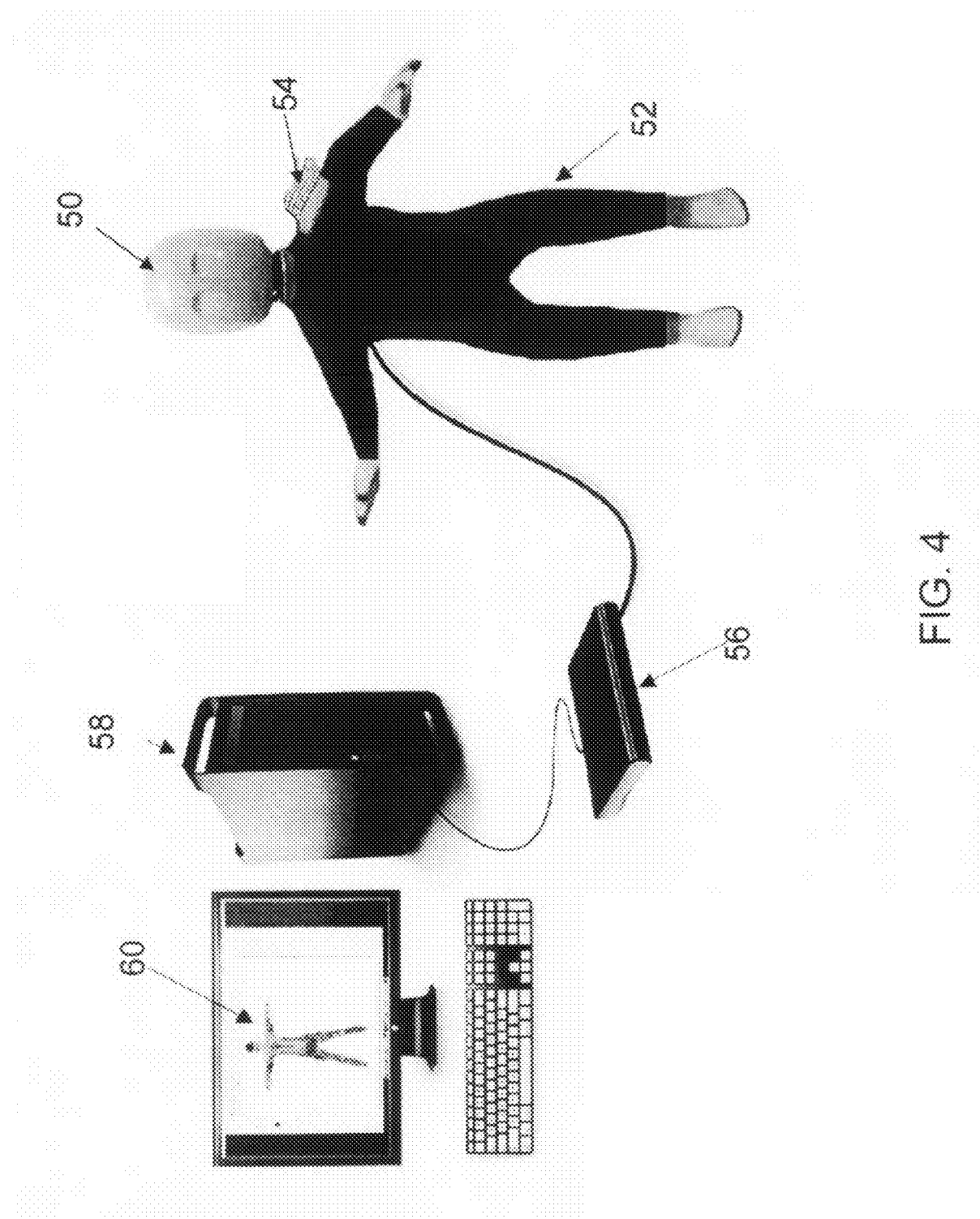
FIG. 4 is an overall schematic drawing of a soft tissue impact assessment system in accordance with an embodiment of the invention.

Another preferred embodiment test assessment system of the invention is illustrated in FIG. 4. An anthropomorphic test dummy or human surrogate 50 having the shape of a human child or adult is fitted with a sensor skin soft tissue impact assessment device 52 like that in FIG. 2 but that is molded into the shape of a full body skin similar to the form of a wet suit. A position and force or pressure sensor sheet 54 is within the device 52 throughout the skin shape of the device. A data acquisition unit 56 receives force or pressure and position measurement data and the data is compiled by software in a computer 58. A display 60 displays a graphical body map image output, such as a color coded mapping in which colors code the magnitude of force or pressure measured at different regions of the anthropomorphic test device or human surrogate 50 during testing.

The invention, including the particular embodiments of the invention described above, has many applications as will be appreciated by artisans. A particular application of the invention is to aid in the protection of parts of the human population that lack the independence or ability to provide the necessary information for professional care givers and protectors. Infants, children and the elderly are examples, and the invention provides for the development of highly specific objective data that can be used to objectively assess the circumstances of the potential for soft tissue injury. The invention also provides a system that can be used by professionals to make an assessment of compatibility between a stated cause of injury and the resulting soft tissue injuries.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A soft tissue impact assessment device, comprising:
   a skin shaped or moldable to a human-like form;
   a positional pressure or force sensor within the skin, the positional pressure or force sensor measuring magnitude of force or pressure, and identifying location of impact or contact with the skin from among a plurality of separate sensor identifiable points of impact or contact with the skin, and further providing data regarding the magnitude of force or pressure and providing data regarding the location of impact or contact with the skin, said skin consisting essentially of,
      a top layer made of a material and thickness that simulates the protection provided by particular human skin to underlying tissue;
      a pressure or force sensor sheet forming said positional pressure or force sensor and contacting the top layer in a manner that avoids any substantial movement between said top layer and said pressure sensor sheet during a range of anticipated force or pressure conditions to be experienced during testing;
      a lining layer suitable to be in close contact with a surface of a human like form.

2. A system for measuring soft tissue impact or contact, the system comprising:
   a soft tissue impact assessment device of claim 1; and
   an output device for displaying information indicating magnitude of force or pressure, and displaying location of the impact or contact with the skin based upon the data provided from said positional or force sensor.

3. The system of claim 2, wherein said output device comprises a graphical user interface for interacting with data from a database.

4. The system of claim 2, wherein said skin is fitted onto or forms part of anthropomorphic test dummy or human surrogate.

5. The system of claim 2, further comprising a computer for generating a body image map describing patterns and numbers of potential bruises or soft tissue injuries associated with specific events detected by said positional pressure or force sensor; wherein said output device outputs the body image map.

6. The device of claim 1 wherein said positional force or pressure sensor comprises a continuous pressure sensitive film that can measure the magnitude of force or pressure and can identify the location of impact or contact with the skin.

7. The device of claim 1 wherein said positional pressure or force sensors comprise an array of individual sensors, each individual sensor providing individual pressure or force data associated with an individual location of said skin.

8. The device of claim 1, wherein said lining layer comprises neoprene.

9. The device of claim 8, wherein said sensor sheet comprises an array of individual sensors, each individual sensor providing individual pressure or force data associated with an individual location of said skin.

10. The device of claim 9, wherein said sensor sheet array is integrally molded to said top layer and said lining layer.

11. The device of claim 1, wherein the device is configured to closely fit around a portion of a human like form.

12. The device of claim 11, wherein the human like form comprises a portion of one of a human infant, human child, and human elderly person.

13. The device of claim 11, wherein the human like form comprises a portion of a human infant.

14. A system for measuring soft tissue impact or contact, the system comprising:
a soft tissue impact assessment device of claim 1; and
a computer receiving data from the device of claim 1, said computer accepting human subject data concerning a soft tissue injury being assessed;
searching a database including objective data concerning the presence of potential soft tissue injuries as described through contact or impact points;
outputting the compatibility between human subject injuries and stated event based upon the matching objective data.

15. The system of claim 14, wherein the subject data is obtained from measurement by the soft tissue impact assessment device.

16. The system of claim 14, wherein the database comprises information organized by:
category of potentially injurious events;
human age; and
objective data relating location and force or pressure level for various events for a given human surrogate a certain population.

17. and the system of claim 14, wherein the searching comprises comparing the subject soft tissue date to the objective data to match the subject soft tissue data to particular categories of injuries and determining compatibility of the subject soft tissue data with an injury event.

18. The device of claim 1, wherein said lining layer contacts an opposite side of pressure or force sensor sheet.

19. The device of claim 1, wherein said skin is flexible and moldable to the contour of the human like form.

20. The device of claim 19, wherein the device is a multi-use device that can be retrofitted over a human like form that is a previously manufactured human surrogate.

21. The device of claim 1, wherein the device is a multi-use device that can be retrofitted over a human like form that is previously manufactured human surrogate.

* * * * *

UNITED STATES PATENT AND TRADEMARK OFFICE
CERTIFICATE OF CORRECTION

PATENT NO. : 8,292,830 B2  
APPLICATION NO. : 12/154166  
DATED : October 23, 2012  
INVENTOR(S) : Gina Bertocci Page 1 of 1

It is certified that error appears in the above-identified patent and that said Letters Patent is hereby corrected as shown below:

In the Specification:

Col. 6, line 16          After "FIG. 1" please insert --.--.

In the Claims:

Col. 8, line 56, Claim 1          Please remove "close".

Signed and Sealed this  
Sixth Day of August, 2013

Teresa Stanek Rea  
*Acting Director of the United States Patent and Trademark Office*